United States Patent
Liu et al.

(10) Patent No.: US 10,576,049 B1
(45) Date of Patent: Mar. 3, 2020

(54) COMPOSITION FOR IMPROVING FUNCTION OF AORTIC ENDOTHELIAL CELL AND USE THEREOF

(71) Applicant: XI'AN JIAOTONG UNIVERSITY, Xi'an (CN)

(72) Inventors: Jian-Kang Liu, Xi'an (CN); Xu-Yun Liu, Xi'an (CN); Tian-Yang Zhang, Xi'an (CN); Zhi-Sheng Ye, Xi'an (CN); Ding-Yi Ye, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 0 days.

(21) Appl. No.: 16/509,503

(22) Filed: Jul. 12, 2019

(30) Foreign Application Priority Data

Nov. 23, 2018  (CN) .......................... 2018 1 1402622

(51) Int. Cl.
| | | |
|---|---|---|
| *A61K 31/185* | (2006.01) | |
| *A61K 31/19* | (2006.01) | |
| *A61P 9/10* | (2006.01) | |
| *A61K 47/34* | (2017.01) | |
| *A61K 47/44* | (2017.01) | |

(52) U.S. Cl.
CPC ............. *A61K 31/19* (2013.01); *A61K 47/34* (2013.01); *A61K 47/44* (2013.01); *A61P 9/10* (2018.01)

(58) Field of Classification Search
CPC ................................................... A61K 31/185
USPC ........................................................ 514/557
See application file for complete search history.

(56) References Cited

U.S. PATENT DOCUMENTS

| | | | |
|---|---|---|---|
| 6,878,733 B1 * | 4/2005 | Shenoy | A61K 9/0019 514/397 |
| 2008/0254011 A1 * | 10/2008 | Rothschild | A61K 35/747 424/93.45 |

FOREIGN PATENT DOCUMENTS

| | | | | |
|---|---|---|---|---|
| WO | WO-2011152803 A1 * | 12/2011 | | A61K 9/0007 |

* cited by examiner

*Primary Examiner* — Raymond J Henley, III

(57) ABSTRACT

The disclosure relates to a composition for improving aortic endothelial cell function and use thereof. The composition includes acetic acid, lactic acid, polyoxyethylene castor oil, and disodium alkyl polyoxyethylene sulfosuccinate. The composition is capable of inhibiting inflammatory response of the human aortic endothelial cells caused by saturated fatty acids, increasing a mitochondrial respiration and metabolism of vascular endothelial cells, and preventing an occurrence and progression of atherosclerosis. The composition is capable of reducing human aortic endothelial inflammation caused by saturated fatty acids, for example, reducing the mRNA levels of interleukin-6 (IL-6) and matrix metalloproteinase-1 (MMP-1), and is capable of effectively protecting the function of mitochondria in human aortic endothelium from being damaged by saturated fatty acids, for example, increasing the expression of mitochondrial complexes I and III and mitochondrial metabolism-associated Foxo1.

3 Claims, 3 Drawing Sheets

Specification includes a Sequence Listing.

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 1
ttttgtactc atctgcacag c                                            21

<210> SEQ ID NO 2
<211> LENGTH: 21
<212> TYPE: DNA
<213> ORGANISM: Artificial Sequence -continued

```
<220> FEATURE:
<223> OTHER INFORMATION: Backward primer for IL-6

<400> SEQUENCE: 2
ggattcaatg aggagacttg c                                      21

<210> SEQ ID NO 3
<211> LENGTH: 19
<212> TYPE: DNA
<213> ORGANISM: Artificial Sequence
<220> FEATURE:
<223> OTHER INFORMATION: Forward primer for MMP-1

<400> SEQUENCE: 3
acgccagatt tgccaagag                                         19

<210> SEQ ID NO 4
<211> LENGTH: 21
<212> TYPE: DNA
<213> ORGANISM: Artificial Sequence
<220> FEATURE:
<223> OTHER INFORMATION: Backward primer for MMP-1

<400> SEQUENCE: 4
ttgaccctca gagaccttgg t                                      21

<210> SEQ ID NO 5
<211> LENGTH: 20
<212> TYPE: DNA
<213> ORGANISM: Artificial Sequence
<220> FEATURE:
<223> OTHER INFORMATION: Forward primer for beta-actin

<400> SEQUENCE: 5
atcatgtttg agaccttcaa                                        20

<210> SEQ ID NO 6
<211> LENGTH: 19
<212> TYPE: DNA
<213> ORGANISM: Artificial Sequence
<220> FEATURE:
<223> OTHER INFORMATION: Backward primer for beta-actin

<400> SEQUENCE: 6
agatgggcac agtgtgggt                                         19
```

COMPOSITION FOR IMPROVING FUNCTION OF AORTIC ENDOTHELIAL CELL AND USE THEREOF

SEQUENCE LISTING

This application contains a Sequence Listing in computer readable form. The computer readable form is incorporated herein by reference.

CROSS-REFERENCE TO RELATED APPLICATION

This application claims all benefits accruing under 35 U.S.C. § 119 from China Patent Application No. 201811402622.1, filed on Nov. 23, 2018 in the State Intellectual Property Office of China, the content of which is hereby incorporated by reference.

FIELD

The present disclosure belongs to the pharmaceutical field, and particularly relates to a composition for improving aortic endothelial cell function and use thereof.

BACKGROUND

Statistical data shows that 17.7 million people die each year from cardiovascular disease, accounting for 31% of all deaths worldwide. This number steadily increases year by year, and it is expected that the mortality caused by cardiovascular disease will be significantly higher than other diseases from 2008 to 2030, taking a lead in causes of death. The pathological basis of cardiovascular diseases and cerebrovascular diseases, such as myocardial infarction and cerebral infarction, is atherosclerosis.

Atherosclerosis, whose pathogenesis is very complex, is a chronic inflammatory response with plaque built inside arteries, and accompanied by damages of vascular endothelial cells. The main factors leading to atherosclerosis are unhealthy diet such as high-salt, high-fat, and high-energy diet, smoking, and metabolic risk factors, including diseases such as "Three-High" symptom (hypertension, hyperglycemia, and hyperlipidemia) and obesity.

At present, atherosclerosis may be treated by medicine and surgery, but is latent leading to a high lethality rate and a high disability rate, upon which a prevention and early treatment of atherosclerosis are particularly favorable. Studies have revealed that natural active ingredients such as chlorogenic acid, "Xiongshao" (*Ligusticum chuanxiong* and *Paeoniae rubra* radix) and lignans have anti-atherosclerotic effects, and functional foods containing these ingredients have been appeared on the market. In view of this, exploring more natural substances that are effective against cardiovascular diseases such as atherosclerosis has a great significance and prospect.

SUMMARY

An object of the present disclosure is to provide a composition for ameliorating aortic endothelial cell function and use thereof.

The composition for ameliorating aortic endothelial cell function is prepared by mixing acetic acid, lactic acid, polyoxyethylene castor oil, and disodium alkyl polyoxyethylene sulfosuccinate.

In one embodiment, the acetic acid, lactic acid, polyoxyethylene castor oil, and disodium alkyl polyoxyethylene sulfosuccinate can be in a mass ratio of 1:2.2:1.8:1.5.

The composition can be used in inhibiting an inflammation of aortic endothelial cells caused by a saturated fatty acid.

The composition can be used in reducing mRNA levels corresponding to interleukin-6 (IL-6) and matrix metalloproteinase-1 (MMP-1) in aortic endothelial cells.

The composition can be used in protecting mitochondria from being damaged by inflammation of aortic endothelial cells caused by a saturated fatty acid.

The composition can be used in increasing an expression of mitochondrial complexes I and III proteins, and mitochondrial metabolism-associated FoxO1 protein.

Another object of the present disclosure is to provide a composition for preventing or treating a cardiovascular disease, and the composition is prepared by mixing acetic acid, lactic acid, polyoxyethylene castor oil, and decanol polyoxyethylene ether sulfosuccinate sodium salt.

In one embodiment, the acetic acid, lactic acid, polyoxyethylene castor oil, and disodium alkyl polyoxyethylene sulfosuccinate can be in a mass ratio of 1:2.2:1.8:1.5.

The composition can be used in treating atherosclerosis.

Another object of the present disclosure is to provide a composition for preventing atherosclerosis, and the composition is prepared by mixing acetic acid, lactic acid, polyoxyethylene castor oil, and decanol polyoxyethylene ether sulfosuccinate sodium salt.

In one embodiment, the acetic acid, lactic acid, polyoxyethylene castor oil, and disodium alkyl polyoxyethylene sulfosuccinate can be in a mass ratio of 1:2.2:1.8:1.5.

Another object of the present disclosure is to provide a medicine or a nutritional supplement comprising any of above-described compositions.

The compositions are capable of inhibiting an inflammatory response of human aortic endothelial cells caused by a saturated fatty acid, increasing respiration and metabolism of mitochondria of vascular endothelial cells, and preventing an occurrence and progress of atherosclerosis by anti-inflammation and protecting the mitochondria.

The compositions are capable of effectively reducing human aortic endothelial inflammation caused by a saturated fatty acid, for example, reducing levels of mRNAs corresponding to interleukin-6 (IL-6) and matrix metalloproteinase-1 (MMP-1) in aortic endothelial cells.

The compositions are capable of effectively protecting the function of the mitochondria in human aortic endothelial cells from being damaged by a saturated fatty acid, for example, increasing an expression of mitochondrial complexes I and III proteins and mitochondrial metabolism-associated Foxo1 protein.

The compositions, medicines, and nutritional supplements have a good application prospect in preventing the occurrence and progress of vascular diseases.

BRIEF DESCRIPTION OF THE DRAWINGS

Implementations are described by way of example only with reference to the attached figures.

FIG. 2A and FIG. 2B are diagrams showing an embodiment of the composition is capable of avoiding a palmitic acid-induced decrease of mitochondrial complexes I and III expressions in human aortic endothelial cells, wherein FIG. 2A shows a Western blot testing result, FIG. 2B is a statistical diagram from the Western blot testing result, the abscissa of FIG. 2B represents the group and the protein name, and the ordinate of FIG. 2B represents relative protein expression level.

FIG. 3A and FIG. 3B are diagrams showing an embodiment of the composition is capable of avoiding a palmitic acid-induced decrease of mitochondrial FoxO1 protein expression in human aortic endothelial cells, wherein FIG. 3A shows a Western blot testing result, FIG. 3B is a statistical diagram from the Western blot testing result, the abscissa of FIG. 3B represents the group, and the ordinate of FIG. 3B represents relative FoxO1 protein expression level.

DETAILED DESCRIPTION

Figure 1:
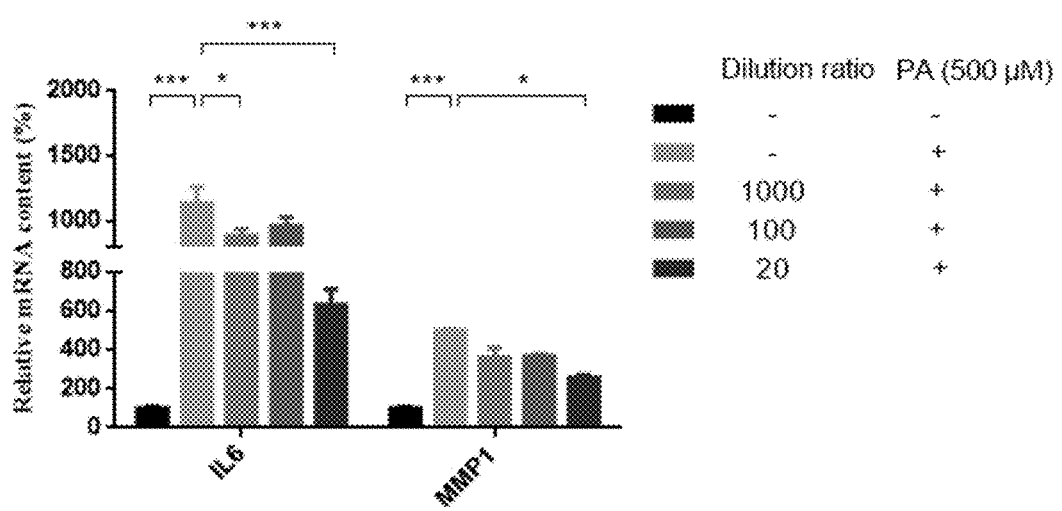
FIG. 1 is a diagram showing inhibitory effects of an embodiment of the composition in different concentrations on palmitic acid-induced inflammation of human aortic endothelial cells, wherein the abscissa represents the group and the concentration of the composition, and the ordinate represents mRNA levels corresponding to IL-6 and MMP-1.

A detailed description with the above drawings is made to further illustrate the present disclosure.

A composition is prepared by mixing acetic acid, lactic acid, polyoxyethylene castor oil, and disodium alkyl polyoxyethylene sulfosuccinate.

In one embodiment, the acetic acid, lactic acid, polyoxyethylene castor oil, and disodium alkyl polyoxyethylene sulfosuccinate can be in a mass ratio of 1:2.2:1.8:1.5.

The CAS number of the polyoxyethylene castor oil is 61791-12-6. In some embodiments, the polyoxyethylene castor oil is selected from one of EL-12, EL-20, and combinations thereof.

In some embodiment, the disodium alkyl polyoxyethylene sulfosuccinate can be $RO(CH_2CH_2O)_nCOCH_2CH(SO_3Na)COONa$ represented by the following structure (I), wherein R can be an alkyl containing 5 to 15 carbon atoms, and n can be in a range from 1 to 10.

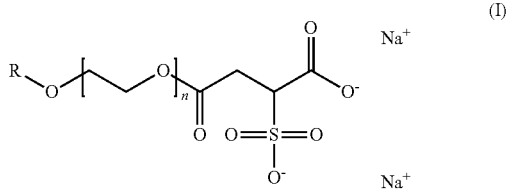

(I)

The alkyl can be a straight chain alkyl or a branched chain alkyl. In some embodiments, R is decanol or dodecyl. In some embodiments, n is 1 to 5. In one embodiment, the CAS number of the disodium alkyl polyoxyethylene sulfosuccinate can be 39354-45-5.

1. Experimental Materials

TRIzol™ reagent was purchased from Invitrogen™. RNA reverse transcription kit and SYBR fluorescent dye were purchased from Takara Biotechnology (Dalian) Co., Ltd. RNA primers were ordered from and synthesized by Xi'an Qingkezexi Bio Co., Ltd.

2. Culture of Experimental Cells and Model Establishment

Human aortic endothelial cells (HAEC) were purchased from Shanghai Baili Biotechnology Co., Ltd. Palmitic acid was purchased from SIGMA Company. The cells were cultured in a constant-temperature, humidified, sterile incubator. The experiments were performed in three experiment groups: I. control; II. 500 μM palmitic acid treatment; and III. composition protecting.

In each of the three experiment groups, the cells were respectively cultured at an atmosphere of 95% air and 5% $CO_2$ at 37° C. in wells of a 12-well cell culture plate for the following mRNA level detection, and in wells of a 6-well cell culture plate for the following protein detection. After the cell density of the three experiment groups were all cultured to 40% to 50%, the composition was added to the cells of group III. The composition was comprised of the acetic acid, lactic acid, polyoxyethylene castor oil (EL-12), and disodium alkyl polyoxyethylene sulfosuccinate (A-102) in the mass ratio of 1:2.2:1.8:1.5. Different concentrations of the composition were obtained by diluting the composition by adding a solvent having a volume of 20, 100, or 1000 times of the composition. The composition in different concentrations was applied to the cells of group III respectively. Then the cells of the three groups were continued to be cultured at the atmosphere of 95% air and 5% $CO_2$ at 37° C. for about 24 hours. After that, 500 μM palmitic acid was respectively added to the cells of group II and group III, followed by culturing at the atmosphere of 95% air and 5% $CO_2$ at 37° C. for about 24 hours.

3. Experimental Methods (1) IL-6 and NMP-1 mRNA Level Detection

The detecting of mRNA levels corresponding to interleukin-6 and matrix metalloproteinase-1 was carried out by using reverse transcription RNA and real-time quantitative polymerase chain reaction (PCR), and the specific method is as follows:

1) RNA Extraction

The medium for cell culture in the wells was removed. 500 μL of TRIzol™ reagent was added to each well of the 12-well cell culture plate having the samples cultured therein, which was then shaken at room temperature for 5 minutes. 200 μl of chloroform was then added to each well for extraction of protein. The samples were then vigorously stirred for 15 seconds, rested for 15 minutes at room temperature, and then centrifuged at a relative centrifugal force of 12,000 g for 10 minutes at 4° C. The upper aqueous phase of each sample was transferred to a new eppendorf (EP) tube, to which isopropanol with a volume equal to the transferred upper aqueous phase was added and uniformly mixed with the transferred upper aqueous phase. The solution was rested for 1 hour at −20° C., and then centrifuged at 12,000 g for 10 minutes at 4° C. The supernatant was discarded, and 1 mL of pre-cooled 75% ethanol was added to the RNA pellet and mixed by pipetting up and down. The solution was centrifuged at 12,000 g for 10 minutes at 4° C., and then the supernatant is discarded. The EP tube containing the RNA pellet was placed on a clean bench for 30 minutes to completely evaporate the ethanol, and the resultant was resuspended in 10 μL of DEPC-treated water to form a total RNA solution for the following reverse transcription. The concentration of the solution was measured by an ultraviolet spectrophotometer.

2) Reverse Transcription of RNA

For performing the reverse transcription, a solution with a total volume of 20 μl was prepared by mixing 2 μg of the extracted RNA, 0.5 μg of random primers, 4 μL of 5× Master Mix, and DEPC-treated water taking all the rest volume. The solution was incubated at 37° C. for 60 minutes to have the reverse transcription reaction to obtain cDNA, then inactivated at 80° C. for 15 seconds, and then stored at −20° C. for later use.

3) Real-Time Quantitative PCR (RT-PCR)

RT-PCR was performed by using the RNA reverse transcription kit and the SYBR fluorescent dye. A system with a total volume of 10 μL was prepared by mixing 1 μL of the obtained cDNA, 5 μL of 2×SYBP®Premix Ex Taq™ II, 0.5 μL of a mixture of forward primer and backward primer (10 μM), and sterilized water taking all the rest volume. The RT-PCR was performed according to instruction of the kit with a protocol as follows: unwinding at 95° C. for 10 minutes; performing PCR for 40 cycles, each of which was performed by sequentially subjecting the system at 95° C. for 30 seconds, at 55° C. for 30 seconds, and at 72° C. for 20 seconds; and finally observing and analyzing a dissociation curve performed by sequentially subjecting the system at 95° C. for 15 seconds, at 60° C. for 15 seconds, and at 95° C. for 15 seconds). β-actin was used as an internal reference, the primer sequences used in the experiment were as follows:

PCR Primers for IL-6:
Forward primer: 5'-TTTTGTACTCATCTGCACAGC-3' (SEQ ID NO: 1)
Backward primer: 5'-GGATTCAATGAGGAGACTTGC-3' (SEQ ID NO: 2)
PCR Primers for MMP-1:
Forward primer: 5'-ACGCCAGATTTGCCAAGAG-3' (SEQ ID NO: 3)
Backward primer: 5'-TTGACCCTCAGAGACCTTGGT-3' (SEQ ID NO: 4)
PCR Primers for β-Actin:
Forward primer: 5'-ATCATGTTTGAGACCTTCAA-3' (SEQ ID NO: 5)
Backward primer: 5'-AGATGGGCACAGTGTGGGT-3' (SEQ ID NO: 6)

(2) Protein Detection

1) Protein Extraction

The medium for cell culture in the wells was removed. 150 μL of IP lysis buffer was added to each well of the 6-well cell culture plat having the samples cultured therein. The cultured cells in the wells were scraped by using a cell scraper, and subjected to vibrating for 15 seconds and cooling in ice bath for 10 minutes, and the vibrating and cooling were repeated three times, ensuring that the cells was ice bathed for at least 30 minutes. Then the samples were centrifuged at 12,000 g for 10 minutes at 4° C. The supernatants were collected, and the proteins therein were quantified by bicinchoninic acid (BCA) assay, and normalized. Then the supernatants were added with 5× loading buffer and mercaptoethanol, and boiled for 10 minutes to denature the proteins. The extracted proteins were stored at −80° C. for later use.

2) Western Blot

10 μg of the extracted proteins containing were subjected to gel electrophoresis with 10% acrylamide gel, and electrophoretic transferred onto a PVDF membrane, which were blocked, and incubated with a primary antibody at 4° C. overnight, free primary antibody was washed away. Then, the membrane was incubated with a secondary antibody at room temperature for 1 hour, and free secondary antibody was washed away. Target proteins were detected by chemiluminescence.

4. Statistical Analysis

Figure 2A:
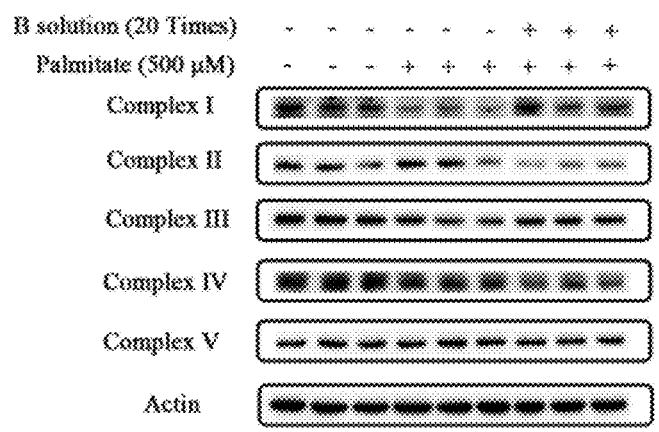
Figure 2B:
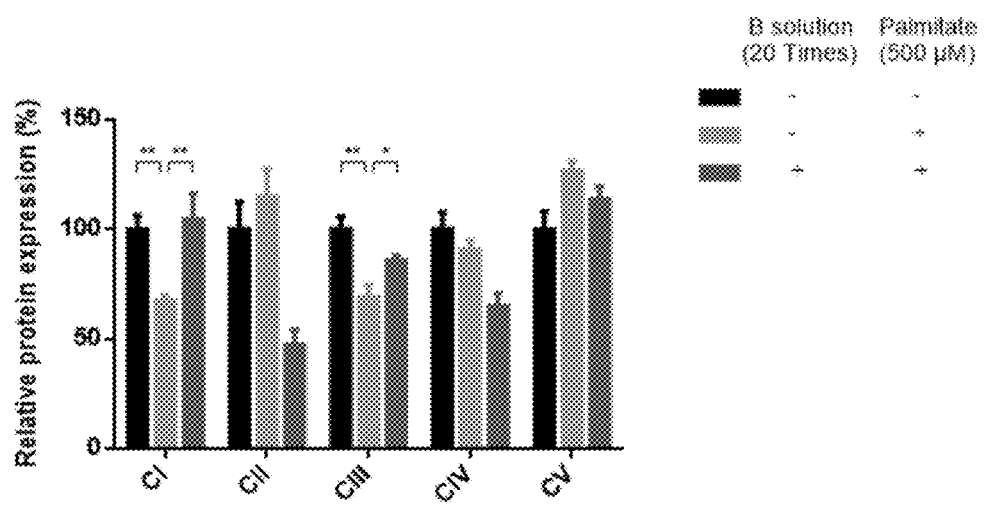
Figure 3A:
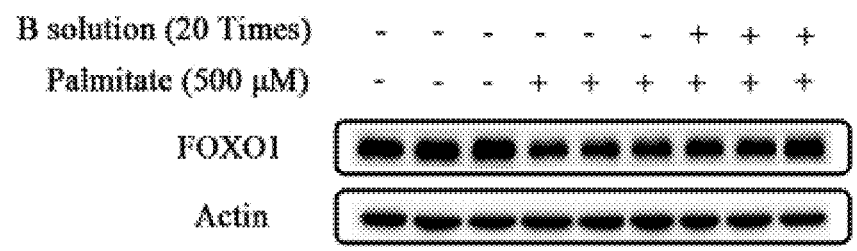
Figure 3B:
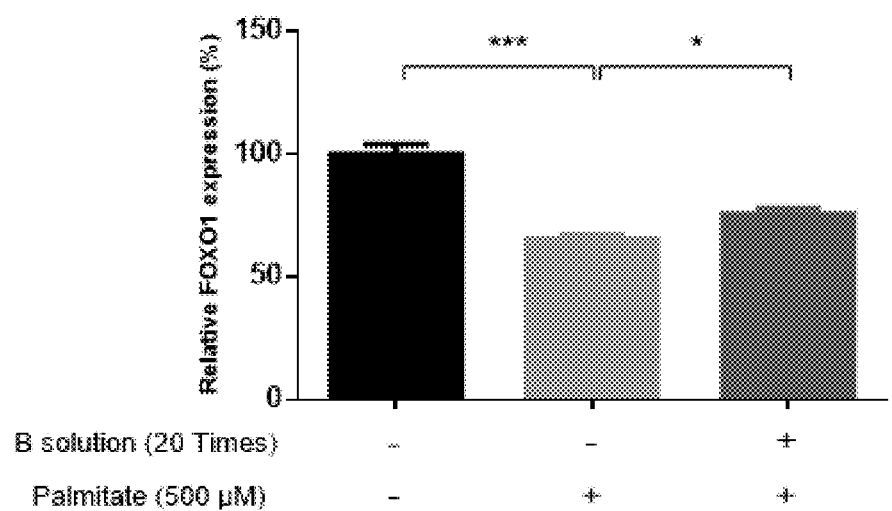

Referring to FIG. 1 to FIG. 3, the data obtained in the above-described experiments, for the amount of the mRNA and the proteins, were expressed in the diagrams in form of mean±SEM (SEM is standard error of mean), and the data were analyzed by using One-way ANOVA analysis method with statistical significance p values of * meaning $p<0.05$,  meaning $p<0.01$, * meaning $p<0.001$.

5. Inhibitory Effect of the Composition of the Present Disclosure on Palmitic Acid-Induced Inflammation of Human Blood Aortic Endothelial Cells Human endothelial cells were first treated with the composition of the present disclosure for 24 hours, and then treated with 500 μM of palmitic acid for 24 hours. FIG. 1 shows that the composition is capable of significantly inhibiting the inflammatory response caused by damage to the human vascular endothelial cells by the palmitic acid. As shown in FIG. 1, 500 μM of palmitic acid induced an inflammatory response in human aortic endothelial cells in the group II, the 500 μM palmitic acid treatment group. The cellular inflammatory factors, interleukin (IL-6) and human matrix metalloproteinase (MMP-1), were significantly higher in the 500 μM palmitic acid treatment group than those in the control group. The mRNA level corresponding to IL-6 was increased for about 12 times, and the mRNA level corresponding to MMP-1 was increased for about 5 times, revealing that the level of inflammation in the model group II, the 500 μM palmitic acid treatment group, was increased significantly. It can be seen from FIG. 1 that by applying 1000 times diluted composition of the present disclosure, the mRNA level corresponding to IL-6 was significantly decreased, revealing a significant inhibition of the inflammatory response. The inhibition effect increases with the concentration of the composition. As shown in FIG. 1, the mRNA levels corresponding to both IL-6 and MMP-1 were significantly decreased by applying 20 times diluted composition of the present disclosure, indicating a significant inhibition effect to the inflammation, and thereby suggesting an anti-inflammation effect and an anti-atherosclerosis effect can be provided by using the composition provided in the present disclosure.

6. Up-Regulating Effect of the Composition of the Present Disclosure on a Palmitic Acid-Induced Decrease of Expression of Mitochondrial Complexes I and III in Human Aortic Endothelial Cells Mitochondrial respiratory chain enzyme is also called as mitochondrial respiratory chain complex or mitochondrial respiratory chain complex enzyme. The mitochondrial respiratory chain is located at inner mitochondrial membrane and composed of 5 complexes, NADH (also called as complex I), succinate dehydrogenase (also called as complex II), cytochrome C oxidoreductase (also called as complex III), cytochrome C oxidase (also called complex IV), and ATP synthase (also called as complex V). Mitochondrial complexes are closely related to electron transport and energy production. A decrease of the expression level of the complexes indicates a deterioration of the mitochondrial function of the cells. FIG. 2A and FIG. 2B show that palmitic acid is capable of reducing the expression of mitochondrial complexes I and III in human aortic endothelial cells, while the composition provided in the present disclosure is capable of significantly increasing the expression of mitochondrial complexes I and III, thereby improving the mitochondrial function of the cells.

7. Up-Regulating Effect of the Composition of the Present Disclosure on a Palmitic Acid-Induced Decrease of Expression of FoxO1 Protein in Human Aortic Endothelial Cells FoxO1 transcription factor, an important member of FoxO subfamily in Fox (Forkhead box) family, is involved in the growth and metabolism of organisms and tumor formation by regulating various physiological processes such as oxidative stress, proliferation, and apoptosis of cells. Foxo1 is also closely related to oxidative stress and mitochondrial production. SOD2 which is a protein against oxidative stress, and PGC-1α which is a mitochondrial-associated protein, are downstream regulatory proteins of the FoxO1 transcription factor. Therefore, a decrease of FoxO1 protein expression in cells will lead to a decrease of the mitochondrial function. FIG. 2A and FIG. 2B show that palmitic acid is capable of reducing the expression of FoxO1 in human aortic endothelial cells, while the composition provided in the present disclosure is capable of significantly increasing the expression of FoxO1, thereby improving the mitochondrial function of the cells.

The above experimental results demonstrate that the composition provided in the present disclosure is capable of effectively inhibiting the inflammatory response and mitochondrial damage of human aortic endothelial cells induced by high fat, thereby improving the function of human aortic endothelial cells.

The composition provided in the disclosure can be used for preparing a medicine or a nutritional supplement for improving aortic endothelial cell function, wherein the composition is prepared by mixing acetic acid, lactic acid, polyoxyethylene castor oil, and decanol polyoxyethylene ether sulfosuccinate sodium salt in a mass ratio of 1:2.2:1.8:1.5.

In some embodiments, the composition can be used as a medicine or a nutritional supplement that inhibits the inflammatory response of aortic endothelial cells caused by a saturated fatty acid.

In some embodiments, the composition can be used as a medicine or a nutritional supplement that reduces the mRNA levels of interleukin-6 (IL-6) and matrix metalloproteinase-1 (MMP-1) in aortic endothelial cells.

In some embodiments, the composition can be used as a medicine or a nutritional supplement that protects mitochondria from being damaged by inflammation of aortic endothelial cells caused by a saturated fatty acid.

In some embodiments, the composition can be used as a medicine or a nutritional supplement that increases the expression of mitochondrial complexes I and III proteins, and mitochondrial metabolism-associated FoxO1 protein.

A dysfunction of endothelial cell is the initial characterization, the reason, and the basis of occurrence and development of atherosclerosis which is a chronic inflammatory response. The occurrence of the inflammatory response is an important cause of atherosclerosis. Meanwhile, it is reported that a damage of the mitochondria may also be one important cause of atherosclerosis since the damage may induce an energy deficiency and function deterioration of endothelial cells. The composition provided in the present disclosure exhibits excellent properties in protecting endothelial cells from inflammation and protecting mitochondria from being damaged in the endothelial cell damage test. Therefore, the composition provided in the present disclosure has a good prospect in prevention of cardiovascular diseases, such as atherosclerosis, that has an endothelial damage caused by high fat. The composition provides a new medical approach for treatment of cardiovascular diseases caused by imbalance of dietary.

The composition provided in the disclosure can be used for preparing a medicine or a nutritional supplement for preventing and treating cardiovascular diseases, wherein the composition is prepared by mixing acetic acid, lactic acid, polyoxyethylene castor oil, and disodium alkyl polyoxyethylene sulfosuccinate in a mass ratio of 1:2.2:1.8:1.5.

In some embodiments, the composition can be used as a medicine or a nutritional supplement that prevents or treats atherosclerosis.

The composition provided in the disclosure can be used for preparing a medicine or a nutritional supplement for preventing atherosclerosis, wherein the composition is prepared by mixing acetic acid, lactic acid, polyoxyethylene castor oil, and disodium alkyl polyoxyethylene sulfosuccinate in a mass ratio of 1:2.2:1.8:1.5.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. A composition for improving aortic endothelial cell function, the composition comprising acetic acid, lactic acid, polyoxyethylene castor oil, and disodium alkyl polyoxyethylene sulfosuccinate.

2. The composition of claim 1, wherein the acetic acid, the lactic acid, the polyoxyethylene castor oil, and the disodium alkyl polyoxyethylene sulfosuccinate are in a mass ratio of 1:2.2:1.8:1.5.

3. A medicine or a nutritional supplement comprising the composition of claim 1.

* * * * *